(12) United States Patent
Ohkoba

(10) Patent No.: US 10,274,744 B2
(45) Date of Patent: Apr. 30, 2019

(54) BIREFRINGENT FILTER UNIT

(71) Applicant: CANON KABUSHIKI KAISHA, Tokyo (JP)

(72) Inventor: Minoru Ohkoba, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 670 days.

(21) Appl. No.: 15/073,977

(22) Filed: Mar. 18, 2016

(65) Prior Publication Data

US 2016/0291342 A1     Oct. 6, 2016

(30) Foreign Application Priority Data

Apr. 1, 2015 (JP) ................................. 2015-075304

(51) Int. Cl.
| | |
|---|---|
| G02B 27/28 | (2006.01) |
| H01S 3/08 | (2006.01) |
| G02B 5/30 | (2006.01) |
| G02B 1/08 | (2006.01) |
| A61B 5/00 | (2006.01) |
| H01S 3/16 | (2006.01) |

(52) U.S. Cl.
CPC .......... G02B 27/288 (2013.01); A61B 5/0095 (2013.01); G02B 1/08 (2013.01); G02B 5/3066 (2013.01); G02B 5/3083 (2013.01); H01S 3/08054 (2013.01); H01S 3/1625 (2013.01); H01S 3/1636 (2013.01)

(58) Field of Classification Search
CPC ...... G02B 27/288; G02B 1/08; G02B 5/3066; G02B 5/3083; A61B 5/0095; H01S 3/08054; H01S 3/1625; H01S 3/1636
See application file for complete search history.

(56) References Cited

U.S. PATENT DOCUMENTS

| | | | | |
|---|---|---|---|---|
| 4,914,664 A | * | 4/1990 | Woodward | H01S 3/1062 372/105 |
| 5,038,360 A | | 8/1991 | Negus et al. | |

(Continued)

FOREIGN PATENT DOCUMENTS

| | | |
|---|---|---|
| CN | 103718396 A | 4/2014 |
| CN | 103915753 A | 7/2014 |

(Continued)

OTHER PUBLICATIONS

Official Action in Chinese Patent Application No. 201610185889.4, dated Nov. 28, 2018 (with English translation).

(Continued)

*Primary Examiner* — Armando Rodriguez
(74) *Attorney, Agent, or Firm* — Venable LLP

(57) ABSTRACT

The birefringent filter unit includes a planar birefringent plate arranged such that the light enters the birefringent plate at an approximate Brewster's angle, a first reflecting member arranged substantially parallel to the birefringent plate to allow the light having passed through the birefringent plate to enter the birefringent plate at the approximate Brewster's angle, and a second reflecting member arranged opposite to the first reflecting member and substantially parallel to the birefringent plate, which allows the light having passed through the birefringent plate after being reflected by the first regulating member to enter the birefringent plate at the approximate Brewster's angle.

11 Claims, 10 Drawing Sheets

(56) References Cited

U.S. PATENT DOCUMENTS

| | | |
|---|---|---|
| 5,164,946 A | 11/1992 | Negus et al. |
| 5,953,154 A | 9/1999 | Akagawa et al. |
| 6,237,417 B1 | 5/2001 | Lonsdale et al. |
| 9,054,490 B2 | 6/2015 | Iwase |
| 2014/0148660 A1 | 5/2014 | Irisawa et al. |
| 2014/0192828 A1* | 7/2014 | Iwase .................. H01S 3/1062 372/20 |

FOREIGN PATENT DOCUMENTS

| | | |
|---|---|---|
| EP | 1 139 146 A2 | 4/2001 |
| EP | 2 063 310 A2 | 5/2009 |
| JP | 2014-150243 A | 8/2014 |
| KR | 2000-0053214 A | 8/2000 |
| KR | 10-0451117 B1 | 11/2004 |

OTHER PUBLICATIONS

Sep. 16, 2016 European Search Report in European Patent Appln. No. 16162151.1.

S.M. Kobtsev, et al., "Application of birefringent filters in continuous-wave tunable lasers: a review," Optics and Spectroscopy, vol. 73, No. 1, Jul. 1992, pp. 114-123.

* cited by examiner

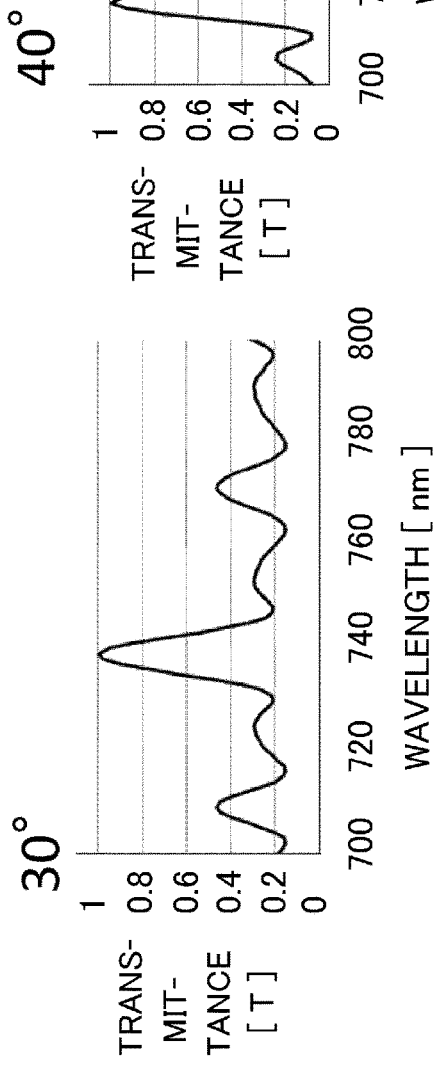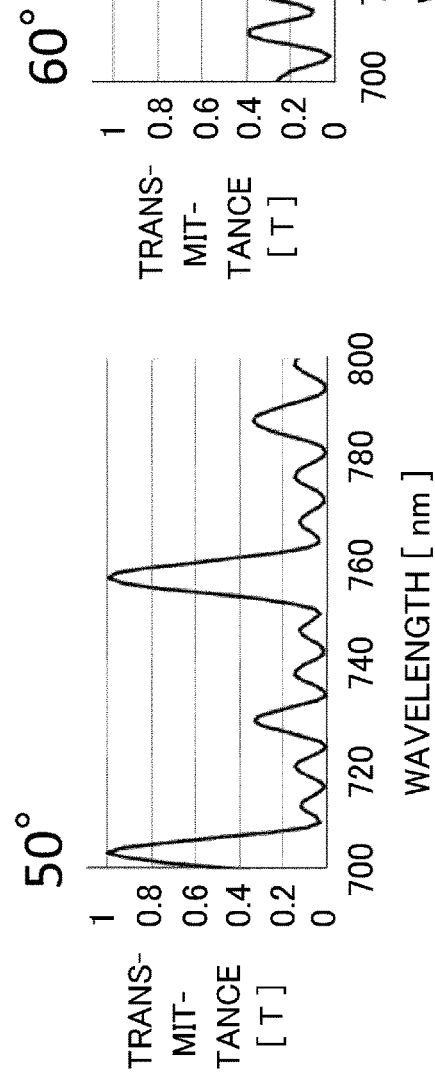
FIG. 9A  FIG. 9B  FIG. 9C  FIG. 9D

BIREFRINGENT FILTER UNIT

BACKGROUND OF THE INVENTION

Field of the Invention

The present invention relates to a birefringent filter unit.

Description of the Related Art

Optical imaging apparatuses are being actively studied in the medical field, which irradiate an organism with light from a light source such as a laser so as to image information relating to the interior of the organism that is obtained based on the light entering the organism. Photoacoustic Tomography (PAT) is one such optical imaging technique. In PAT, an organism is irradiated with pulsed light generated by a light source, and an acoustic wave generated in the organism tissue, which has absorbed the energy of the pulsed light having propagated and diffused through the organism, is detected. This phenomenon of the generation of a photoacoustic wave is referred to as a photoacoustic effect, and an acoustic wave resulting from the photoacoustic effect is referred to as a photoacoustic wave. A segment to be examined such as a tumor often has a higher light energy absorptance compared to surrounding tissues and thus absorbs a larger amount of light than the surrounding tissues and instantaneously expands. An acoustic wave detector is used to detect a photoacoustic wave generated during this expansion to obtain a reception signal. The reception signal is mathematically analyzed to allow imaging of the sound pressure distribution, in the object, of the photoacoustic wave resulting from the photoacoustic effect (the resultant image is hereinafter referred to as a photoacoustic image). Based on the photoacoustic image thus obtained, an optical-characteristic distribution (particularly an absorption coefficient distribution) in the organism can be acquired. Such information can also be utilized to quantitatively measure certain substances in the object, such as glucose or hemoglobin contained in the blood. Currently, photoacoustic image apparatuses are being actively studied which use PAT and are intended to image blood vessels in small animals or be applied to diagnoses of breast cancer or the like.

In-vivo substances such as glucose and hemoglobin vary in light absorptance depending on the wavelength of incident light. Therefore, the distribution of in-vivo substances can be accurately measured by irradiating an organism with light having different wavelengths and analyzing resultant differences in absorption coefficient distribution. In general, light with a wavelength of 500 nm to 1,200 nm is used as irradiation light. In particular, when absorption by melanine or water needs to be avoided, near infrared light with a wavelength of 700 nm to 900 nm is used as incident light.

An alexandrite laser and a titanium sapphire laser are wavelength variable lasers having gain bands in the above-described wavelength range. Examples of a wavelength selection method for the wavelength variable laser include a method of rotating a mirror in a laser resonator with a wavelength dispersion element such as a prism or a diffraction grating arranged therein, a method of using a birefringent filter that is arranged in a laser resonator, and a method of utilizing an acoustic optical element. The birefringent filter method uses a member including a number of birefringent plates (thin plates of birefringent optical elements) arranged parallel to one another so as to be mutually spaced apart by spacers or the like. The optical axes of the birefringent plates lying in the respective planes of the plates are arranged in such a particular angular relation as allows a desired wavelength to be selected. When a wavelength is selected, the whole birefringent filter is rotated with the angular relation maintained and with surfaces of the birefringent plates kept parallel to one another (Japanese Patent Application Laid-open No. 2014-150243).

The number of birefringent plates that is suitable for improving a wavelength selection characteristic is, for example, three (S. M. Kobtsev et al., "Application of birefringent filters in continuous-wave tunable lasers: a review", Optics and Spectroscopy 73(1), 114-123, July 1992).

SUMMARY OF THE INVENTION

It is a difficult operation to align optical axes of a plurality of (for example, three) birefringent plates used for a birefringent filter in the respective planes in a particular direction. It is also a difficult operation to fix the birefringent plates to one another so as to keep the birefringent plates parallel to one another. When bonding is used for the fixation, the axes may be misaligned with one another during hardening of an adhesive.

On the other hand, when the fixation is performed without bonding, the axes may be misaligned with one another by vibration after the fixation. As described above, it is difficult to fix a plurality of birefringent plates while having the optical axes aligned in a particular direction, and to maintain this fixed state. Such a configuration may extend an operation time and increase management costs.

The present invention has been developed in view of the above-described problems. An object of the present invention is to provide a birefringent filter unit that is simply configured and that is easy to manage.

The present invention provides a birefringent filter unit that allows selection of a wavelength for light passing through an optical path, the birefringent filter unit comprising:

a planar birefringent plate arranged such that light traveling on the optical path enters the birefringent plate at an approximate Brewster's angle;

a first reflecting member arranged substantially parallel to the birefringent plate to reflect the light having passed through the birefringent plate, such as to allow the light to enter the birefringent plate at the approximate Brewster's angle; and a second reflecting member arranged opposite to the first reflecting member across the birefringent plate and substantially parallel to the birefringent plate to reflect the light having passed through the birefringent plate after being reflected by the first reflecting member, such as to allow the light to enter the birefringent plate at the approximate Brewster's angle.

The present invention can provide a birefringent filter unit that is simply configured and that is easy to manage.

Further features of the present invention will become apparent from the following description of exemplary embodiments with reference to the attached drawings.

BRIEF DESCRIPTION OF THE DRAWINGS

FIGS. 9A to 9D are diagrams illustrating changes in transmittance in Embodiment 4.

DESCRIPTION OF THE EMBODIMENTS

Figure 1:
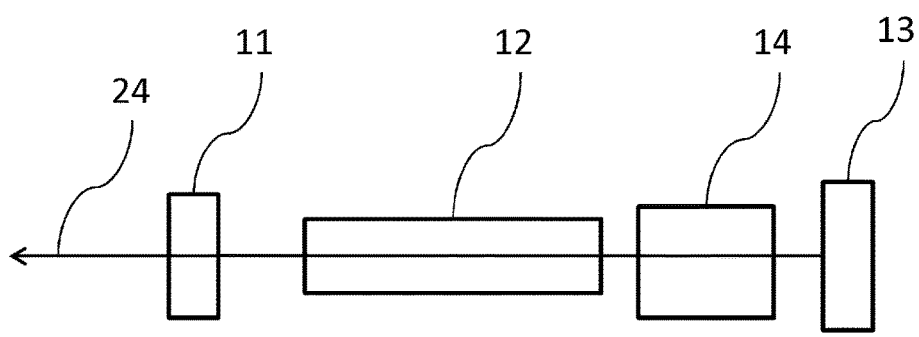
FIG. 1 is a diagram depicting a laser resonator.

With reference to the drawings, preferred embodiments of the present invention will be described below. However, the dimensions, materials, shapes, and relative arrangements of components described below should be changed according to configurations of and various conditions for apparatuses to which the invention is applied. Thus, the dimensions, materials, shapes, and relative arrangements of the components are not intended to limit the scope of the present invention to the following description.

The present invention is considered to be a birefringent filter unit and a method for manufacturing the birefringent filter unit. The present invention is also considered to be a wavelength variable laser apparatus with the birefringent filter unit and a method for controlling the wavelength variable apparatus. Further, the present invention is applicable to a photoacoustic apparatus that uses a wavelength variable apparatus as a light source.

Such a photoacoustic apparatus irradiates an object with light to receive a photoacoustic wave generated inside the object by a photoacoustic effect and propagating through the object and obtains characteristic information relating to the interior of the object based on the photoacoustic wave, in the form of image data or the like. Thus, the photoacoustic apparatus is also referred to as an object information acquiring apparatus. The characteristic information in the object information acquiring apparatus refers to a source distribution of a photoacoustic wave resulting from light irradiation, an initial sound pressure distribution in the object, an optical-energy absorption density distribution and an absorption coefficient distribution derived from the initial sound pressure distribution, and a concentration distribution of a substance forming a tissue. Specifically, the characteristic information is an oxidized or reduced hemoglobin concentration distribution, a blood component distribution such as an oxygen saturation distribution obtained therefrom, or the distribution of fat, collagen, or moisture.

The photoacoustic wave as used herein is typically an ultrasonic wave and includes an elastic wave referred to as a sound wave or an acoustic wave. The acoustic wave resulting from the photoacoustic effect is referred to as a photoacoustic wave. An electric signal into which an acoustic wave is converted by a probe or the like is also referred to as an acoustic signal.

General Configuration (Laser Resonator)

A laser resonator will be described which is a configuration that forms a particular optical path in the present invention. The laser resonator depicted in FIG. 1 includes an output coupler 11, a laser medium 12, a rear mirror 13, and a birefringent filter unit 14. An optical path 24 is defined by the configuration of the laser resonator.

(Output Coupler)

The output coupler 11 retrieves a part of light from inside the resonator to outside thereof and returns the remaining part of the light into the resonator. The output coupler 11 is suitably a mirror formed of a dielectric multilayer film or the like and adjusted to have an appropriate reflectance for light with a desired wavelength.

(Laser Medium)

When an object is an organism, a laser apparatus irradiates the object with light with a wavelength at which the light is absorbed by a particular component of the organism. The laser medium 12 used has a gain at particular wavelengths. For example, when light absorption by melanine or water is to be avoided, a laser medium such as an alexandrite crystal or a titanium sapphire crystal is used which enables near infrared light with a wavelength of 700 nm to 900 nm. For crystal laser media, end faces may be formed to incline at a Brewster's angle in order to make oscillation of p-polarized light dominant. A pigment can also be utilized as a laser medium. When light is vertically incident, an anti-reflection film is preferably arranged which includes a dielectric multilayer film corresponding to light with the desired wavelength.

(Rear Mirror)

The rear mirror 13 is a reflector arranged at an end of the resonator opposite to the output coupler 11. The rear mirror 13 is generally formed of a dielectric multilayer film with a reflectance of 95% or more.

(Optical Path)

The optical path 24 is a light propagation path defined by the output coupler 11 and the rear mirror 13 and along which light reciprocates through the resonator. A part of the optical path 24 extends linearly from the output coupler 11 to the outside of the resonator. Light on the optical path substantially vertically enters the output coupler 11 and the rear mirror 13. FIG. 1 depicts a light propagation path in which light on the optical path vertically enters an end face of the laser medium 12. On the other hand, when the optical path is not perpendicular to the end face of the laser medium 12, light is refracted in accordance with a refractive index of the laser medium 12 while propagating through the laser medium 12. When an optical element is arranged on the optical path, the propagation direction changes according to the refractive index and reflectance of the optical element. For convenience, in the description below, when light reciprocates on the optical path 24, one of the traveling directions is referred to as a forward path, whereas the other is referred to as a backward path. When a coordinate system is depicted in the figures, an optical path in a direction of an increase on a z axis corresponds to the forward path, whereas an optical path in the opposite direction corresponds to the backward path.

The optical path for the birefringent filter unit need not necessarily be formed in the resonator. To produce the effects of the present invention, the optical path may meet the following requirements. Light propagating through the optical path is within a particular range of wavelengths. Light travels in a straight line within a particular range of divergence angles. Light spreads over a particular area. Light reciprocates through the optical path. A polarization state is not disturbed during reciprocation. An optical path meeting these requirements is referred to as a "particular optical path".

(Birefringent Filter Unit)

Figure 2A:
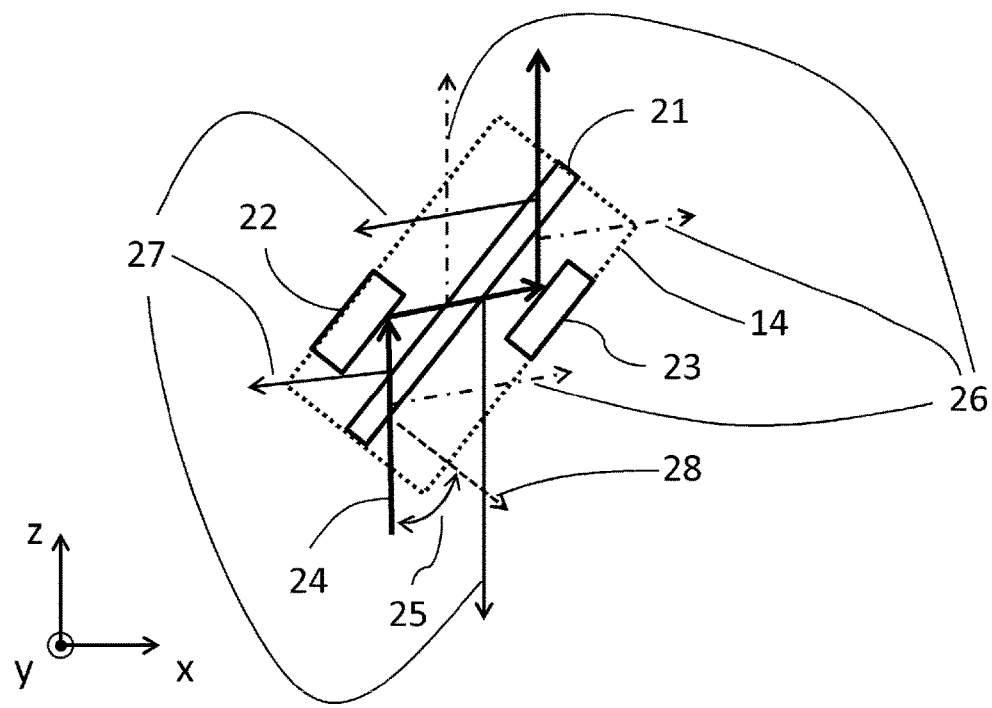
FIGS. 2A and 2B are diagrams depicting a birefringent filter unit.
Figure 2B:
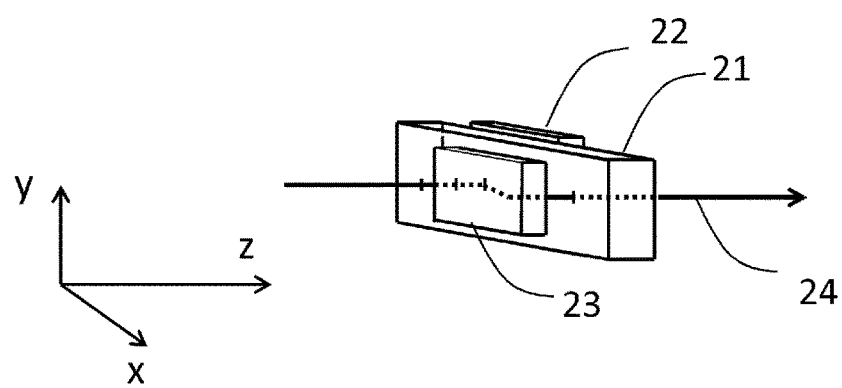

Now, the birefringent filter unit 14 according to the present invention will be described using a top view in FIG. 2A and a perspective view in FIG. 2B. The birefringent filter unit 14 includes a birefringent plate arranger 21, a first reflecting member 22, and a second reflecting member 23. The optical path is denoted by reference numeral 24. An incident angle to the birefringent plate arranger is denoted by reference numeral 25. Reflected light on the forward path of the optical path is denoted by reference numeral 26. Reflected light on the backward path of the optical path is denoted by reference numeral 27. A plane orientation of a birefringent plate (a tangential direction of the birefringent plate) is denoted by reference numeral 28.

(Birefringent Plate Arranger)

The birefringent plate arranger 21 includes a birefringent plate that is a planar thin plate of an anisotropic optical element (for example, a rock crystal or quartz) and a mechanical member that supports the birefringent plate. A feature of the present invention is that the reflecting members move to allow light to enter and pass through the birefringent plate three times at an approximate Brewster's angle. A specific manner of orienting the optical axis of the birefringent plate is selected to make p-polarized light higher than s-polarized light in transmittance through the birefringent plate at a predetermined wavelength. A specific manner of determining the direction of the optical axis of the birefringent filter unit is similar to a parallel, contiguous arrangement of three birefringent plates described in prior literatures.

The members are arranged so as to make the angle of the optical path to the plane orientation (tangential direction) 28 of the birefringent plate, that is, the incident angle 25 of light, equal to the Brewster's angle at which the transmittance for p-polarized light is maximized (reflectance for p-polarized light is zero).

A method for arranging the members so as to make the incident angle equal to the Brewster's angle will be described below. The reflectance for polarized light is a value depending on wavelength and angle as represented by Expressions (1) and (2).

$$r_p = \sin(\theta_2 - \theta_1)/\sin(\theta_2 + \theta_1) \tag{1}$$

$$r_s = \tan(\theta_2 - \theta_1)/\tan(\theta_2 + \theta_1) \tag{2}$$

In the expressions, a p-polarized light reflectance is denoted by $r_p$. An s-polarized light reflectance is denoted by $r_s$. The incident angle of light is denoted by $\theta_1$. The angle between the traveling direction in the birefringent plate and the plane orientation (tangential direction) of the birefringent plate is denoted by $\theta_2$. For isotropic members, the $r_p$ and $r_s$ can be calculated using the $\theta_1$ and $\theta_2$ determined by Snell's law. On the other hand, for anisotropic birefringent plates, the reflectance varies depending on the direction of the optical axis in the plane, leading to the need to execute calculations for refraction related to the optical axis actually used.

By way of example, a case will be discussed where light with a wavelength of 750 nm is allowed to enter a birefringent plate formed of a rock crystal with the optical axis thereof lying in the plane of the plate. In this case, the reflectance in the optical-axis direction (ordinary-light refractive index) is 1.539, whereas the reflectance in a direction perpendicular to the optical axis direction (extraordinary-light refractive index) is 1.548. For such a birefringent plate for which the ordinary-light refractive index is different from the extraordinary-light refractive index, the optical axis is rotated in the plane, preventing the Brewster's angle from being uniquely determined. However, in the present invention, this angle is considered not to vary significantly, and an average value for the ordinary-light refractive index and the extraordinary-light refractive index is used to calculate the Brewster's angle. When the average value (approximately 1.54) is applied to the above-described expressions to determine an energy reflectance spectrum, the p-polarized light reflectance is found to be minimized (a p-polarized light transmittance is found to be maximized) at approximately 57 degrees. Hence, when a rock crystal is used, the incident angle 25 is approximately 57 degrees.

In the present invention, for an allowable range within which sufficient wavelength selection performance can be exhibited, the approximate Brewster's angle is defined as the angle at which the reflectance for p-polarized light is approximately 1% or less (57 degrees±7 degrees). When a birefringent plate other than the rock crystal is used, the approximate Brewster's angle may also be set based on the wavelength of light, the ordinary- and extraordinary-light refractive indices, and the desired wavelength selection performance. In general, the refractive index of the birefringent plate actually used for the present object is often approximately 1.5 to 1.8.

(First Reflection Member)

As the first reflecting member, a member is used which does not disturb a polarization direction or disturb a relation between the incident angle and the reflection angle. For example, the first reflecting member is a metal mirror, a mirror with a dielectric film, or a prism. When light is reflected by the first reflecting member, both the incident angle and the reflection angle are equal to the Brewster's angle. As a result, reflected light from the first reflecting member enters the birefringent plate arranger again at the Brewster's angle. The first reflecting member has a planar reflection surface, and the reflection surface and the birefringent plate may be arranged substantially parallel to each other.

(Second Reflection Member)

A material suitable for the second reflecting member is similar to the material for the first reflecting member. When light is reflected by the second reflecting member, both the incident angle and the reflection angle are equal to the Brewster's angle, as is the case with the first reflecting member. As a result, reflected light from the second reflecting member also enters the birefringent plate arranger again at the Brewster's angle. Hence, the second reflecting member is arranged opposite to the first reflecting member across the birefringent plate. The second reflecting member also has a planar reflection surface, and the reflection surface and the birefringent plate may be arranged substantially parallel to each other.

Now, a positional relation between each of the members and the optical path will be described with reference back to FIG. 2. In FIG. 2, thick arrows represent a forward optical transmission path, and light in the backward path travels in a direction opposite to the direction of the arrows. Part of light entering the resonator through the optical path 24, that is, light traveling through the forward path, is reflected by the birefringent plate in the birefringent plate arranger 21 to turn into the reflected light 26 on the forward path. Part of incident light traveling through the backward path is also reflected by the birefringent plate to turn into the reflected light 27 on the backward path.

Components of the reflected light are mostly s-polarized light removed to allow for wavelength selection. The reflected light traveling onto the optical path again may impair a wavelength selection function. Thus, the first and second reflecting members are preferably arranged at positions where no reflected light is incident. At least one of the first and second reflecting members is arranged at such a position. For simplification, FIG. 2 only depicts front surface reflections observed when the reflected light 26 passes through the birefringent plate. However, in actuality, back surface reflections are present. Furthermore, in actuality, multiple reflections occur where reflected light from a back surface of the birefringent plate is subjected to a front surface reflection again. However, the probability of this reflectance is several percent, and thus, light reflected by the birefringent plate twice or more insignificantly affects the wavelength selection performance. Thus, for light reflected by the birefringent plate, only single reflections will be considered below.

(Effects)

In the above-described birefringent filter, p-polarized light passes through the birefringent plates three times in one way on the optical path. The birefringent filter is rotated with the angular relation with the optical axis maintained to allow light with the desired wavelength to be radiated. The use of such a birefringent filter enables inexpensive manufacturing of a laser apparatus that is suitable for photoacoustic apparatuses and that is simply configured and that is easy to manage. The first and second reflecting members are arranged in areas where the reflected light 26 and 27 from the birefringent plate is not incident. Thus, no reflected light is mixed into the optical path, inhibiting the wavelength selection performance from being impaired.

(Management Method)

Now, maintenance of the birefringent filter will be discussed. When light passing through the birefringent filter decomposes organic substances in an atmospheric gas, a growing foreign matter in a solid state referred to as "haze" may be formed on a surface of the birefringent plate. The foreign matter diffuses light, and thus, in the case of laser light, disadvantageously increases an oscillation threshold, while reducing the wavelength selection performance. The foreign matter can be removed using a cleaning step. However, for a birefringent filter with a plurality of (for example, three) birefringent plates joined together, removal of haze based on the cleaning fails to be achieved unless the birefringent plates are temporarily disassembled. Then, in reassembly following the disassembly and cleaning, accurately aligning the optical axes of the birefringent plates in the appropriate direction is a difficult operation. On the other hand, the above-described configuration includes the single birefringent plate and is thus easy to manage and has improved maintenance performance.

Embodiment 1

Figure 3:
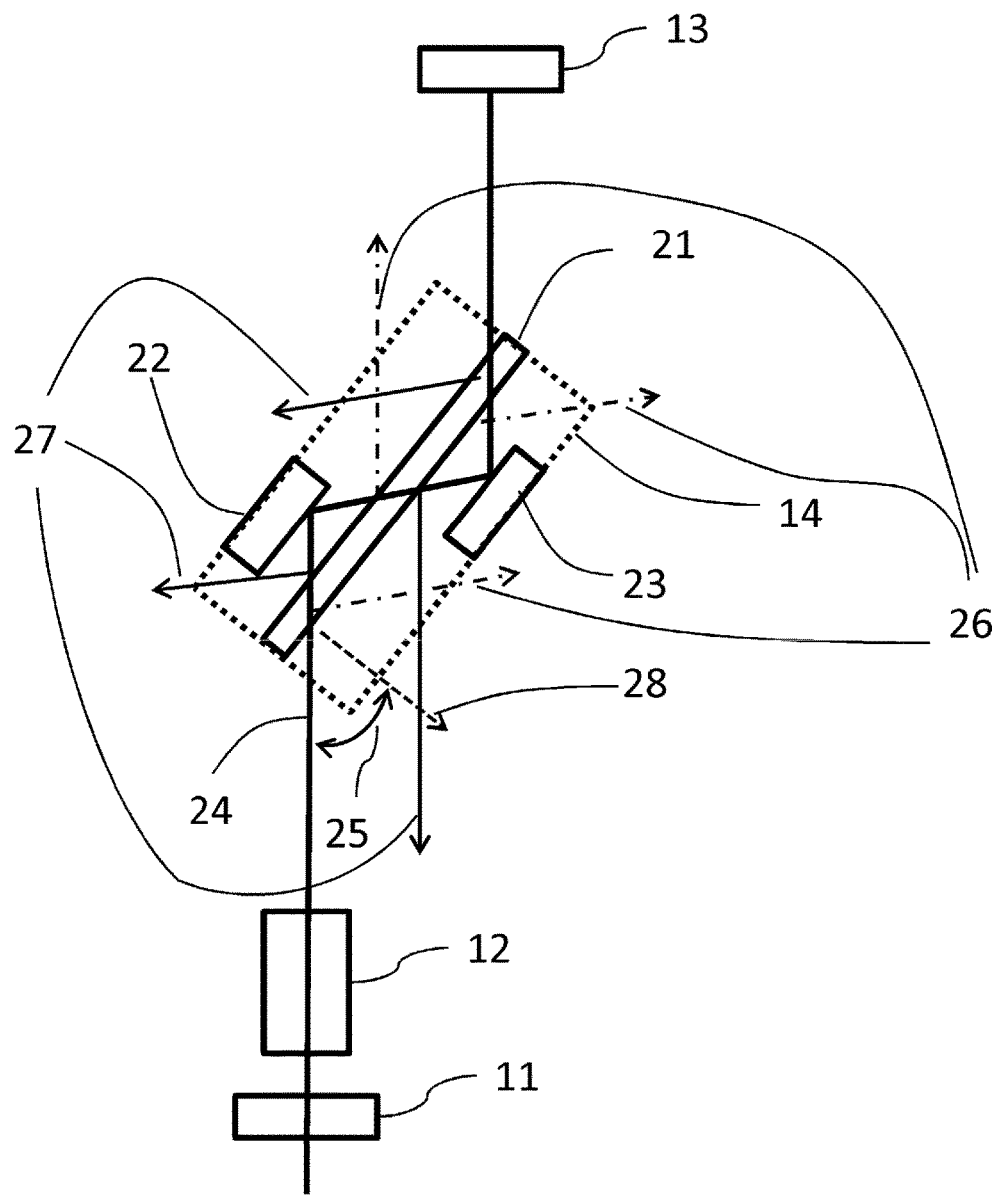
FIG. 3 is a diagram illustrating Embodiment 1.

Embodiment 1 will be described using FIG. 3. Components in FIG. 3 that are common to FIG. 1 and FIG. 2 are denoted by the same reference numerals and will not be described below. The laser medium 12 is a titanium sapphire crystal and has end faces cut so as to be perpendicular to light with which the crystal resonates. A crystal axis is formed to allow p-polarized light to pass through. The output coupler 11 includes a dielectric film with a transmittance of 50%. The rear mirror 13 includes a dielectric multilayer film with a reflectance of 99%. A xenon lamp is utilized as an excitation source (not depicted in the drawings) to excite the laser medium to form an optical path 24 with a sectional area of φ4 mm in the resonator.

The birefringent plate arranged in the birefringent plate arranger 21 is a single rock crystal plate. The optical axis of the rock crystal lies in the plane of the birefringent plate. The birefringent plate is arranged such that the in-plane axis of the optical axis has a rotation angle of 48.4 degrees. Therefore, the optical axis is inclined through 48.4 degrees to a direction perpendicular to the sheet. As described above, when the rock crystal and light with a wavelength of 750 nm are used, the Brewster's angle determined from the average refractive index (approximately 15.4) of the ordinary-light refractive index and the extraordinary-light refractive index is 57 degrees. Consequently, the members are arranged so as to set the incident angle 25 to 57 degrees. The size of the rock crystal is 1 mm in thickness, 40 mm in width, and 10 mm in height.

The first reflecting member and the second reflecting member are reflection mirrors each shaped like a rectangular parallelepiped that is 10 mm square and 5 mm thick. The mirrors have a reflectance of 99%. The reflecting members are arranged such that the center of light on the optical path enters the center of a 10-mm×10-mm square surface of each of the reflecting members. This allows reflected light from the birefringent plate to be prevented from entering the reflecting members. Moreover, a clearance of 5 mm is set between each of the reflecting members and the birefringent plate arranger 21 to enable the haze on the surfaces to be removed. Consequently, management is facilitated. The sizes and widths of the mirror and the rock crystal may be changed as needed.

Figure 4:
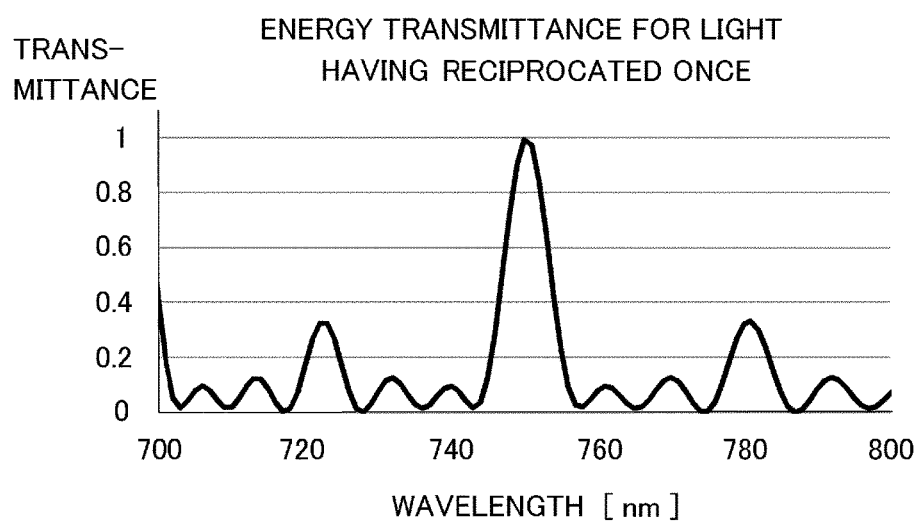
FIG. 4 is a diagram illustrating an energy transmittance resulting from one reciprocation of light in Embodiment 1.

FIG. 4 illustrates the wavelength selection effect of the birefringent filter unit produced in accordance with the above-described method. The axis of abscissas represents the wavelength. The axis of ordinate represents a relative value for the transmittance (the energy transmittance for light having reciprocated once through the resonator). FIG. 4 illustrates a steep transmission peak at a wavelength of 750 nm, indicating high wavelength selection performance. A clearance of 5 mm is present between the birefringent plate arranger 21 and each of the reflecting members, allowing possible haze to be easily removed. Furthermore, the use of the single birefringent plate eliminates the need to align optical axes, allowing a simple configuration to be achieved.

(Variations)

Figure 5:
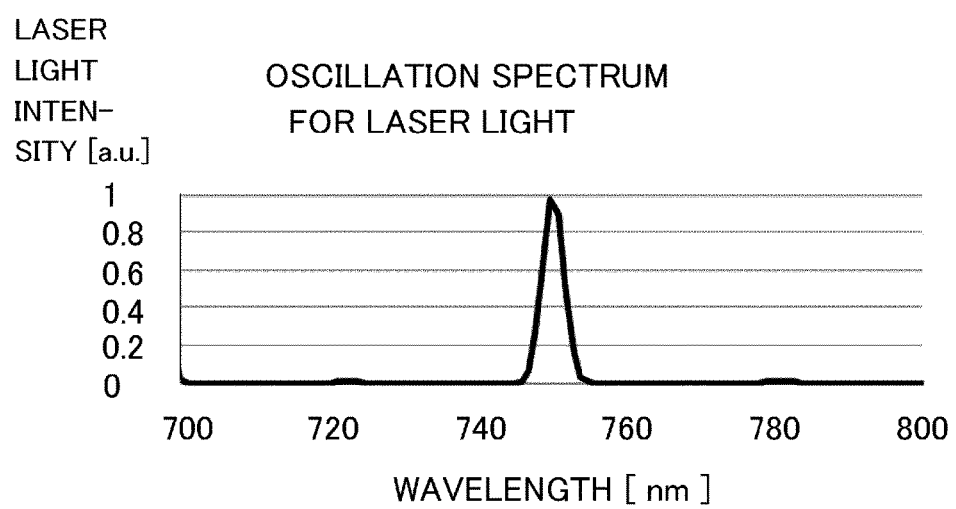
FIG. 5 is a diagram illustrating the energy transmittance in a variation.

In the above description, the wavelength selection capability for light passing through the resonator is evaluated in terms of the transmittance as depicted in FIG. 4. However, an oscillation characteristic of laser light may be noted as depicted in FIG. 5. In FIG. 5, the axis of abscissas represents the wavelength, and the axis of ordinate represents a light intensity (relative value) of a laser apparatus including the birefringent filter unit. Light oscillated by the laser medium passes through the birefringent filter unit each time the light reciprocates a plurality of times through the resonator. Subsequently oscillated laser light has an increased wavelength resolution and a reduced wavelength linewidth. Thus, a laser apparatus including the birefringent filter unit in the present invention exhibits high performance in terms of wavelength selection capability and wavelength linewidth.

Embodiment 2

Figure 6A:
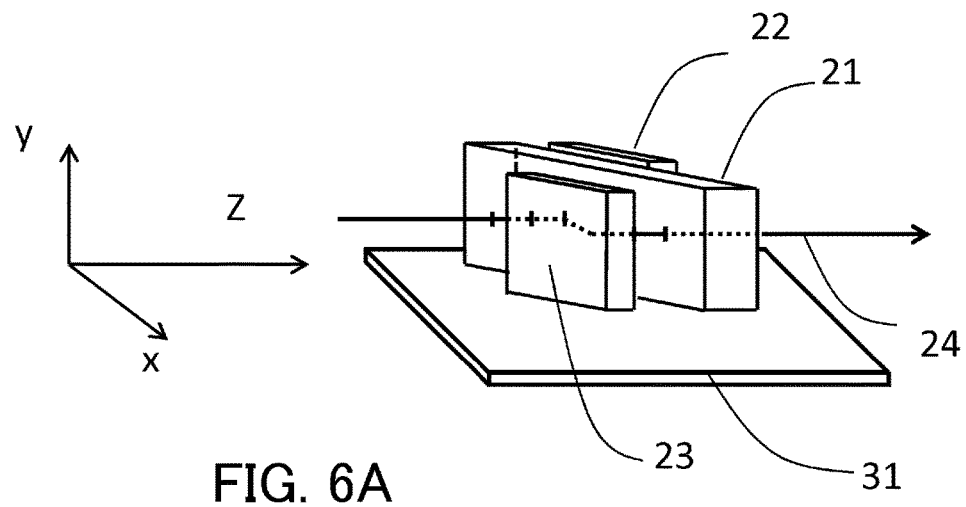
FIGS. 6A and 6B are diagrams illustrating Embodiment 2.
Figure 6B:
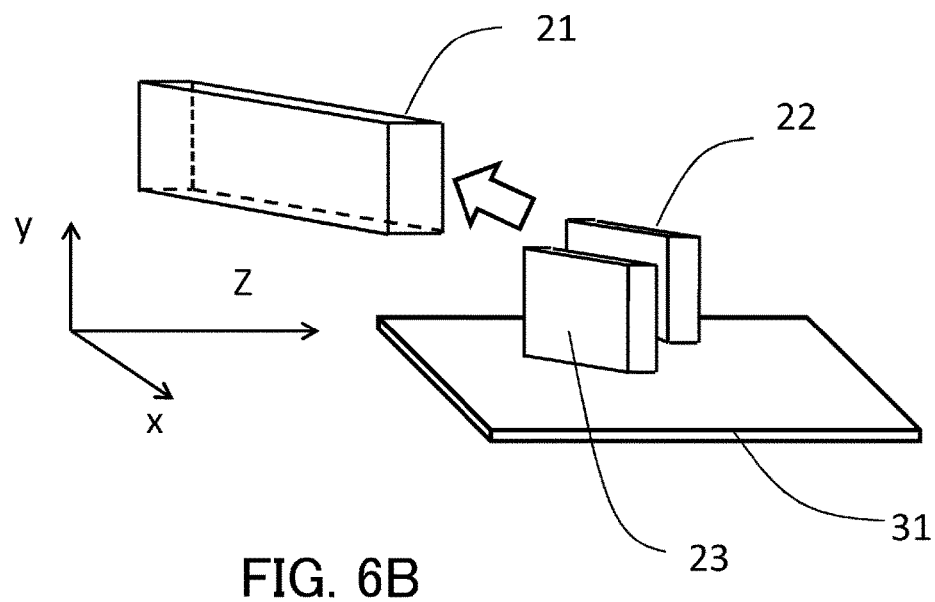

Embodiment 2 will be described with reference to FIG. 6. The birefringent filter in the present embodiment includes a birefringent filter unit stage 31. FIG. 6A illustrates that the birefringent plate arranger is installed on the birefringent filter unit stage 31. FIG. 6B illustrates that the birefringent plate arranger is removed from the birefringent filter unit stage 31.

Embodiment 2 is different from Embodiment 1 in that the birefringent plate arranger 21 can be removed from the birefringent filter unit stage 31. That is, when light irradiation is performed, the birefringent plate arranger 21 is fixed as depicted in FIG. 6A. On the other hand, for maintenance such as haze removal, the birefringent plate arranger 21 is removed as depicted in FIG. 6B. Consequently, haze attached to the birefringent plate can be easily removed.

Furthermore, maintenance time can be shortened by preparing the same birefringent plate arranger 21, and at the time of maintenance, replacing the members in use with the spare members.

Embodiment 3

Figure 7A:
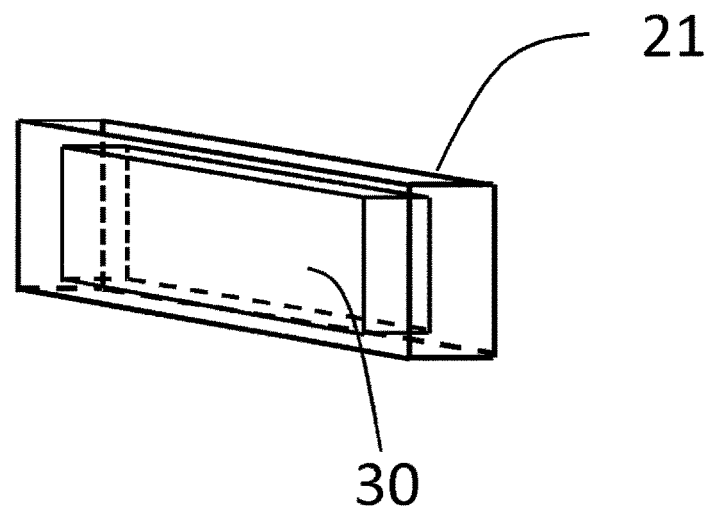
FIGS. 7A and 7B are diagrams illustrating Embodiment 3.
Figure 7B:
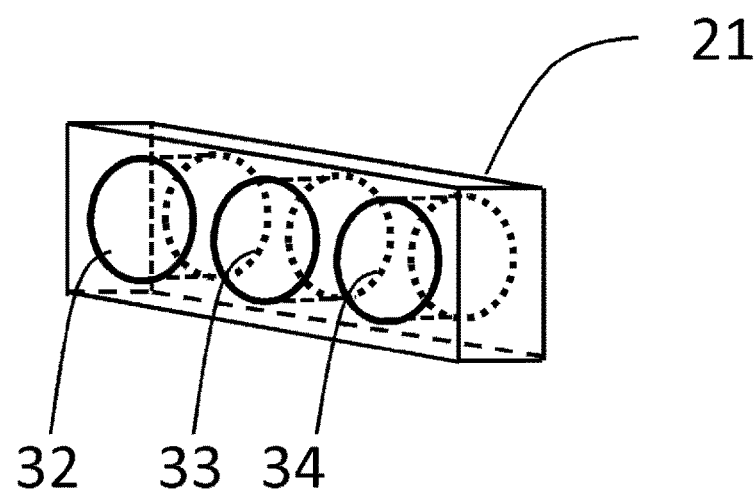

Embodiment 3 will be described with reference to FIG. 7. FIG. 7A depicts the birefringent plate arranger 21 used in Embodiment 1 and including a birefringent plate 30; the birefringent plate arranger 21 is illustrated as a comparison target. FIG. 7B depicts the birefringent plate arranger 21 in Embodiment 3. In the birefringent plate arranger 21 in FIG. 7, a first birefringent plate 32, a second birefringent plate 33, and a third birefringent plate 34 are arranged.

In Embodiment 1, in one way on the optical path, light enters the single birefringent plate 30 three times, which is provided in the birefringent plate arranger 21 and shaped like a rectangular parallelepiped. On the other hand, in Embodiment 3, light enters the small, first to third birefringent plates shaped like cylinders, once in one way on the optical path. This configuration reduces the needed amount of the birefringent plates, enabling a reduction in costs.

(Variations)

In Embodiment 3 depicted in FIG. 7B, the three birefringent plates have a substantially uniform thickness. However, the birefringent plates may have different thicknesses. That is, when two birefringent plates other than the thinnest birefringent plate have thicknesses that are integral multiples of the thickness of the thinnest birefringent plate, adjustment to the desired wavelength linewidth can be easily achieved.

Embodiment 4

Figure 8A:
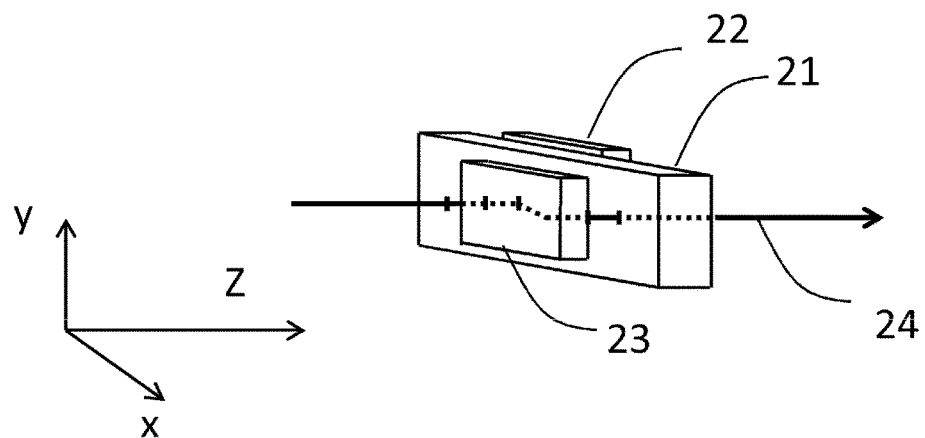
FIGS. 8A and 8B are diagrams illustrating Embodiment 4.
Figure 8B:
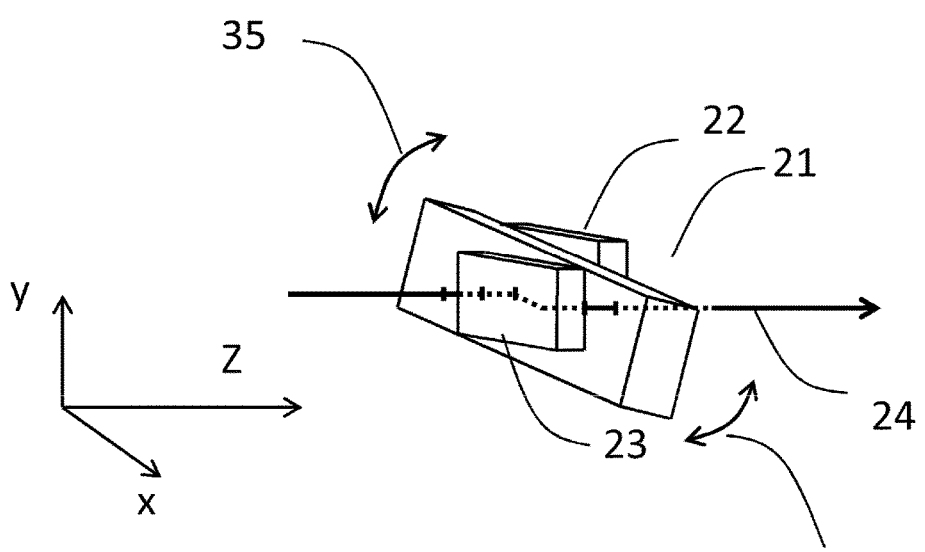

Embodiment 4 will be described using FIG. 8. FIG. 8A depicts the birefringent plate arranger in Embodiment 1 as a comparison target. FIG. 8B depicts the birefringent plate arranger in the present embodiment. A rotating direction of the birefringent plate arranger is denoted by reference numeral 35. The remaining part of the present embodiment is the same as the configuration depicted in FIG. 2B.

A feature of the present embodiment is that the whole birefringent plate arranger rotates with the plane orientation of the birefringent plate (a normal direction of the birefringent plate) in the birefringent plate arranger maintained. As depicted in FIGS. 8A and 8B, the parallel relation between the birefringent plate arranger and each of the first and second reflecting members is maintained. This enables a change in the angle of the optical axis for light passing through the birefringent plate. The center of rotation is provided at such a position as inhibits the optical path from being blocked at each position taken by the birefringent plate as a result of rotation. To reduce the area of the birefringent plate, the center of the plate is desirably aligned with the center of rotation.

FIGS. 9A to 9D illustrate changes in the transmittance of the birefringent plate observed when the optical axis is rotated in the normal direction of the plane. In this case, a reference (0 degree) is a direction perpendicular to the sheets of FIGS. 9A to 9D. For example, FIG. 9A illustrates that, for an angle of 30 degrees, a transmittance spectrum with a peak near a wavelength of 740 nm is formed, indicating appropriate wavelength selection performance. The oscillation wavelength of laser light is determined according to factors such as a reflection spectrum for the mirrors (11 and 13), which determines a resonant length for laser light, and a gain spectrum for the laser medium, besides the transmittance spectrum.

As rotation control means for the birefringent plate, a known physical driving unit can be utilized such as a member including a motor or a stage. When a planar birefringent plate with the optical axis thereof lying in the plane of the plate is rotationally moved, the optical axis is rotated in the plane. The rotation control means preferably has a memory and a control circuit configured to automatically set a relation between a desired frequency and angle setting for the birefringent filter unit to enable operations. Furthermore, the wavelength of irradiation light is preferably controlled according to a measurement target for the object information acquiring apparatus. For example, when oxygen saturation is measured, light with wavelengths characteristically absorbed by oxidized hemoglobin and reduced hemoglobin is selected.

Rotation of the whole birefringent plate arranger as in the present embodiment allows the angle of the optical axis to be changed to a desired value. As a result, the transmittance spectrum for the birefringent plate changes to increase wavelength selectability.

Embodiment 5

Figure 10A:
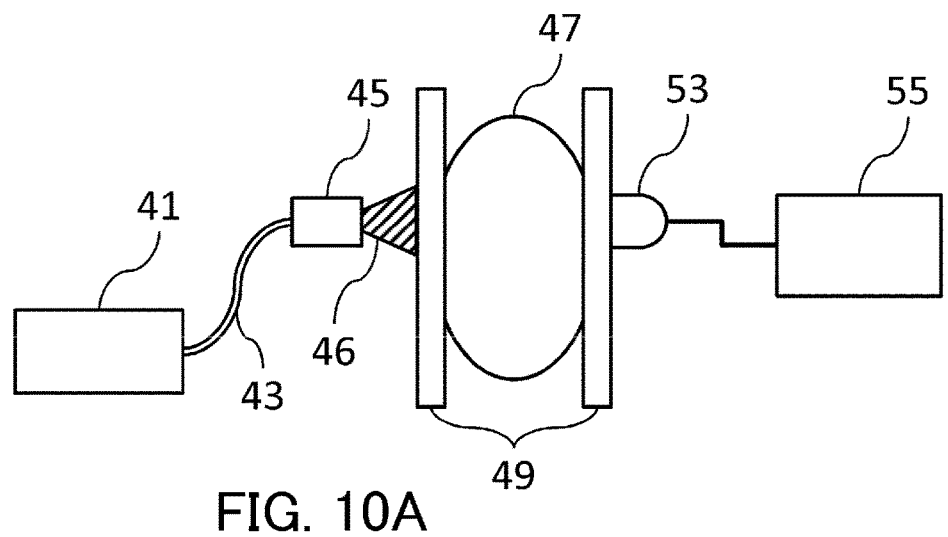
FIGS. 10A and 10B are diagrams illustrating Embodiment 5.
Figure 10B:
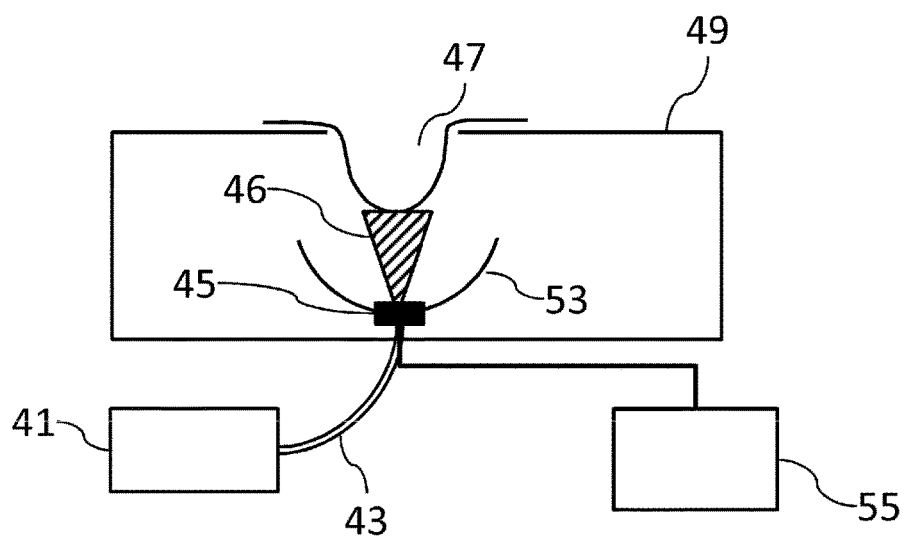

FIGS. 10A and 10B illustrate an example in which a laser apparatus including the above-described birefringent filter is applied to an object information acquiring apparatus that uses the photoacoustic effect. The object information acquiring apparatus has a laser apparatus 41 including the birefringent filter unit in one of the above-described embodiments, an optical transmitter 43, a light irradiator 45, holders 49 that hold an object, an acoustic wave detector 53, and a signal processor 55. The light irradiator 45 radiates irradiation light 46 to an object 47 corresponding to a measurement target.

In the object information acquiring apparatus in FIG. 10A, the object 47 is held between the two plate-like holders 49. The holder 49 located on aside irradiated with light allows light to pass through. The holder 49 located on a side with the acoustic wave detector 53 arranged thereon allows acoustic waves to pass through. As the holders 49, polymethylpentene resin of thickness 10 mm may be used. The acoustic wave detector 53 may be irradiated with light from behind. A combination of optical members such as a bundle fiber, a waveguide, a mirror, and a prism is preferably used as the optical transmitter 43, which propagates light from a light source.

An irradiation position and an irradiation area for the irradiation light 46 are adjusted by an optical system (such as a lens) provided in the light irradiator 45 so as to guide the light onto the object 47 at a front surface of the acoustic wave detector 53. The acoustic wave detector 53 and the light irradiator 45 preferably perform photoacoustic measurement while being moved synchronously via mechanical scan means, to obtain data from a wide range of the object. A gap between the acoustic wave detector 53 and the holder 49 is filled with an acoustic matching material (water, gel, castor oil, or the like).

The laser apparatus 41 in the present embodiment oscillates laser light of wavelength 750 nm, pulse width approximately 50 nsec, and pulse energy approximately 200 mJ as illustrated in Embodiment 1. The acoustic wave detector 53 includes transducers arranged in a two-dimensional array of 15×10 transducers and each including a detection element with an element size of 2 mm square, an element pitch of 2 mm, and a central detection frequency of 1 MHz. The detection elements are capable of receiving and converting an acoustic wave into an analog electric signal. Any detection elements may be used such as piezoelectric elements, Fabry-Perot elements, or capacitance elements.

The signal processor 55 executes an amplification process, a digital conversion process, an image reconstruction process, or the like on a time series of electric signals received by the acoustic wave detector 53. An existing algorithm such as phasing addition, Fourier transform, or filtered back projection may be applied to the image reconstruction. Thus, photoacoustic image data on the interior of the object is generated. As the signal processor, an information processing apparatus is used as needed which includes various electric circuits and a CPU that executes arithmetic processes in accordance with programs. Photoacoustic images may be displayed on a display (not depicted in the drawings) or stored in a memory as image data.

FIG. 10B depicts a form in which a bowl-shaped acoustic wave detector 53 is used. The object 47 (for example, a subject's breast) is inserted through an opening between the holders 49, shaped like a housing, into a space between the holders 49 filled with the acoustic matching material. In this case, a cup-shaped member may be provided to support the object. In the acoustic wave detector 53, the detection elements are arranged in a bowl-shaped probe. In the center of a bottom surface of the probe, the light irradiator 45 is provided through which light from the laser apparatus 41 is radiated. Preferably, the probe performs light irradiation and acoustic-wave reception while moving with respect to the object 47. The remaining parts of the configuration and the signal processing are similar to the corresponding parts illustrated in FIG. 10A.

As described above, in the object information acquiring apparatus that uses the photoacoustic effect, the birefringent filter unit in the present invention is adopted for the laser serving as a light source, to allow the optical axis to be appropriately adjusted. Thus, high-definition images can be acquired. Furthermore, the configuration is simple, allowing maintenance such as haze removal to be easily performed and enabling an increase in stable operation time during measurement.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-075304, filed on Apr. 1, 2015, which is hereby incorporated by reference herein in its entirety.

What is claimed is:

1. A birefringent filter unit that allows selection of a wavelength for light passing through an optical path, the birefringent filter unit comprising:
    a planar birefringent plate arranged such that light traveling on the optical path enters the birefringent plate at an approximate Brewster's angle;
    a first reflecting member arranged substantially parallel to the birefringent plate to reflect the light having passed through the birefringent plate, such as to allow the light to enter the birefringent plate at the approximate Brewster's angle; and
    a second reflecting member arranged opposite to the first reflecting member across the birefringent plate and substantially parallel to the birefringent plate to reflect the light having passed through the birefringent plate after being reflected by the first reflecting member, such as to allow the light to enter the birefringent plate at the approximate Brewster's angle.

2. The birefringent filter unit according to claim 1, wherein at least one of the first reflecting member and the second reflecting member is arranged at a position where the light reflected by the birefringent plate is not incident.

3. The birefringent filter unit according to claim 1, wherein each of the first reflecting member and the second reflecting member is arranged at a position where the light reflected by the birefringent plate is not incident.

4. The birefringent filter unit according to claim 1, wherein the birefringent plate can be removed from the birefringent filter unit.

5. The birefringent filter unit according to claim 1, further comprising a birefringent plate arranger in which the birefringent plate is arranged.

6. The birefringent filter unit according to claim 1, wherein the birefringent plate arranger rotates the birefringent plate in the plane.

7. The birefringent filter unit according to claim 1, wherein the birefringent plate has an optical axis in the plane.

8. The birefringent filter unit according to claim 7, wherein the birefringent plate is a rock crystal.

9. A resonator comprising:
    a laser medium;
    a rear mirror;
    an output coupler; and
    the birefringent filter unit according to claim 1.

10. A laser apparatus comprising:
    the resonator according to claim 9; and
    an excitation source that excites the laser medium,
    wherein the rear mirror and the output coupler form the optical path through which laser light oscillated by excitation of the laser medium reciprocates.

11. An object information acquiring apparatus comprising:
    the laser apparatus according to claim 10;
    an acoustic wave detector that converts an acoustic wave generated by an object irradiated with light from the laser apparatus into an electric signal; and a signal processor that uses the electric signal to acquire characteristic information relating to an interior of the object.

\* \* \* \* \*